United States Patent [19]

Berg et al.

[11] Patent Number: 4,735,690

[45] Date of Patent: * Apr. 5, 1988

[54] DEHYDRATION OF IMPURE FORMIC ACID BY EXTRACTIVE DISTILLATION

[76] Inventors: Lloyd Berg; An-I Yeh, both of 1314 S. Third Ave., Bozeman, Mont. 59715

[*] Notice: The portion of the term of this patent subsequent to Jun. 16, 2004 has been disclaimed.

[21] Appl. No.: 860,648

[22] Filed: Apr. 28, 1986

Related U.S. Application Data

[63] Continuation-in-part of Ser. No. 838,263, Mar. 10, 1986, abandoned.

[51] Int. Cl.$^4$ .......................... B01D 3/40; C07C 53/02
[52] U.S. Cl. ........................................ 203/51; 203/15; 203/56; 203/57; 203/58; 203/60; 203/61; 203/62; 203/63; 203/65; 562/609
[58] Field of Search ...................... 203/15, 16, 14, 57, 203/51, 58, 63, 60–62, 56; 562/609, 606, 608

[56] References Cited

U.S. PATENT DOCUMENTS

| | | | |
|---|---|---|---|
| 3,951,755 | 4/1976 | Sartorius et al. | 203/60 |
| 4,024,028 | 5/1977 | Haskell | 203/57 |
| 4,076,594 | 2/1978 | Buelow et al. | 203/58 |
| 4,217,460 | 8/1980 | Hohenschutz et al. | 562/609 |
| 4,262,140 | 4/1981 | Bott et al. | 562/609 |
| 4,576,683 | 3/1986 | Cohen | 203/15 |

FOREIGN PATENT DOCUMENTS 156309 10/1985 European Pat. Off. ............ 562/609

*Primary Examiner*—Wilbur Bascomb

[57] ABSTRACT

Impure formic acid cannot be completely removed from formic acid-water-impurity mixtures by distillation because of the presence of the maximum azeotrope between formic acid and water. Formic acid can be readily removed from mixtures containing it, water and impurities of the ether, ester, ketone or diketone type by using extractive distillation in which the extractive agent is a higher boiling oxygenated, nitrogenous or sulfur containing organic compound or a mixture of these. Examples of effective agents are adiponitrile; sulfolane and salicyclic acid; dimethylformamide, N,N-dimethylacetamide and ethylene glycol ethyl ether acetate.

2 Claims, No Drawings

DEHYDRATION OF IMPURE FORMIC ACID BY EXTRACTIVE DISTILLATION

This application is a continuation in part of application Ser. No. 838,263 filed Mar. 10, 1986 which has been abandoned.

FIELD OF THE INVENTION

This invention relates to a method for dehydrating impure formic acid using certain higher boiling liquids as the agent in extractive distillation.

DESCRIPTION OF PRIOR ART

Extractive distillation is the method of separating close boiling compounds or azeotropes by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixture and the extractive agent are continuously removed from the column. The usual methods of separation of these two components are the use of another rectification column, cooling and phase separation or solvent extraction.

There are currently two commercial methods for manufacturing formic acid. One is the reaction of caustic soda with carbon monoxide under pressure to produce sodium formate. This is then hydrolysed with sulfuric acid to yield the formic acid. The other is to obtain the formic acid as a by-product from the oxidation of n-butane. Both of these processes yield an aqueous mixture of formic acid. However the components of this mixture cannot be separated by conventional rectification because formic acid boils at 100.8° C., only 0.8° C. above water and because these two form a maximum azeotrope boiling at 107.2° C. and containing 22.5 wt.% water. Thus it is impossible to separate completely formic acid from water by rectification because of the closeness of the boiling points and because as soon as the maximum azeotrope composition is attained, no further change in composition will occur.

Both of the manufacturing processes described above produce an impure formic acid. In the butane oxidation process, formic acid is one of about forty identified products and a very minor one at that. The impurities that are the most troublesome are those which do not react with formic acid, are soluble in formic acid and formic acid-water mixtures, but not in water. Those compounds such as hydrocarbons, are insoluble in both formic acid and water and are separated by decantation. Those compounds which are soluble in both formic acid and water can sometimes be separated by conventional rectification when they boil at temperatures sufficiently greater or less than 107.2° C., the boiling point of the formic acid-water maximum azeotrope. Those compounds that are soluble in formic acid but insoluble in water can remain with the formic acid while it is being concentrated by distillation. Some water and water soluble impurities are removed as the formic acid is concentrated toward its maximum azeotrope.

Extractive distillation would be an attractive method of effecting the separation of formic acid from water if agents can be found that (1) will break the formic acid-water azeotrope and (2) are easy to recover from formic acid, that is, form no azeotrope with formic acid and boil sufficiently above formic acid to make the separation by rectification possible with only a few theoretical plates.

Extractive distillation typically requires the addition of an equal amount to twice as much extractive agent as the formic acid-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent may be miscible with formic acid otherwise it will form a two-phase azeotrope with the formic acid in the recovery column and some other method of separation will have to be employed.

The breaking of this azeotrope by extractive distillation is a new concept. Recent attempts to separate formic acid from water were reported by Kokai, Japanese Pat. No. 82 24,324, Feb. 8, 1982 who used amines or phosphate esters to separate formic acid from water. Kawabata, Higuchi and Yoshida, J. Bull. Chem. Soc. Japan, 1981, 54(11), 3253–8 used poly(4-vinylpyridine) to remove the water from formic acid. Jahn, East German Pat. No. 133,559, Jan. 10, 1979 separated acetic acid-formic acid-water mixtures in three successive columns and only got a partial dehydration of the formic acid.

OBJECTIVE OF THE INVENTION

The object of this invention is to provide a process or method of extractive distillation that will enhance the relative volatility of water from formic acid in their separation in a rectification column. It is a further object of this invention to identify suitable extractive distillation agents which will eliminate the formic acid-water azeotrope and make possible the production of pure formic acid and water by rectification. It is a further object of this invention to identify organic compounds which are stable, can be separated from formic acid by rectification with relatively few plates and can be recycled to the extractive distillation column and reused with little decomposition. It is a fourth object of this invention to find extraction distillation agents which in addition to the above constraints, will remove impurities in addition to water from the formic acid.

SUMMARY OF THE INVENTION

The objects of the invention are provided by a process for separating impure formic acid from water which entails the use of certain oxygenated, nitrogenous or sulfur containing organic compounds, some alone but principally as mixtures, as the agent in extractive distillation.

DETAILED DESCRIPTION OF THE INVENTION

We have discovered that a number of organic compounds, either alone or in mixtures, will effectively negate the formic acid-water maximum azeotrope and permit the separation of water from formic acid by rectification when employed as the agent in extractive distillation. We also discovered that if the formic acid contained an impurity which is soluble in formic acid but not soluble in water, it will accompany the water in the overhead product and on condensation to the liquid phase, form two layers. Table 1 lists several sulfones and their mixtures and the approximate proportions that we have found to effective. Table 3 lists successful agents containing adiponitrile; Table 4, methyl glutaronitrile; Table 5, dimethylformamide; Table 6, formamide; Table 7, N,N-dimethylacetamide and Table 8, several miscellaneous agents. The data in Table 1 was obtained in a vapor-liquid equilibrium still. In each case, the starting material was the formic acid-water azeotrope. The ratios are the parts by weight of extractive agent used per part of formic acid-water azeotrope. The relative volatilities are listed for each of the two ratios employed. The compound which is effective when used alone is sulfolane. The compounds which are effective when used in mixtures are dimethyl sulfone, phenyl sulfone, dihydroxydiphenyl sulfone, butadiene sulfone, adiponitrile, methyl glutaronitrile, phenyl acetic acid, salicylic acid, acetophenone and benzophenone. The two relative volatilities shown in Table 1 correspond to the two different ratios investigated. For example, in Table 1, one part of sulfolane with one part of the formic acid-water azeotrope gives a relative volatility of 2.11, 6/5 parts of sulfolane give 2.04. One half part of sulfolane mixed with one half part of adiponitrile with one part of the formic acid-water azeotrope gives a relative volatility of 3.28, 3/5 parts of sulfolane plus 3/5 parts of adiponitrile give 3.93. One third part of dimethyl sulfone plus ⅓ part of adiponitrile plus ⅓ part of acetophenone with one part of the formic acid-water azeotrope gives a relative volatility of 3.37, with 2/5 parts, these three give a relative volatility of 2.90. In every example in Table 1, the starting material is the formic acid-water azeotrope which possesses a relative volatility of 1.00.

One of the compounds, sulfolane, listed in Table 1 and whose relative volatility had been determined in the vapor-liquid equilibrium still, was then evaluated in a glass perforated plate rectification column possessing 4.5 theoretical plates and the results are listed in Table 2. The data in Table 2 was obtained in the following manner. The charge was 85 wt.% formic acid and 15% water and after a half hour of operation in the 4.5 theoretical plate column to establish equilibrium, sulfolane at 95° C. and 20 ml/min. was pumped in. The rectification was continued with sampling of overhead and bottoms after one hour. The analysis is shown in Table 2 and was 99.5% water, 0.5% formic acid in the overhead and 26.1% water, 73.9% formic acid in the bottoms which gives a relative volatility of 4.09 of water to formic acid. This indicates that the maximum azeotrope has been negated and separation accomplished. Without the extractive agent, the overhead would have approached the maximum azeotrope composition of 22.5% water. This proves that the extractive agent is negating the azeotrope and makes the rectification proceed as if the azeotrope no longer existed and brings the more volatile component, water, out as overhead. And this from formic acid which normally boils only 0.8° C. higher. It is our belief that this is the first time that this has been accomplished for this azeotrope.

TABLE 1

Extractive Distillation Agents Containing Sulfones

| Compounds | Ratios | | Relative Volatilities | |
|---|---|---|---|---|
| Sulfolane | 1 | 6/5 | 2.11 | 2.04 |
| Sulfolane, Adiponitrile | $(1/2)^2$ | $(3/5)^2$ | 3.28 | 3.93 |
| Sulfolane, Methylglutaronitrile | " | " | 2.79 | 3.28 |
| Sulfolane, Phenyl acetic acid | " | " | 1.80 | 1.97 |
| Sulfolane, Salicylic acid | " | " | 3.63 | 4.94 |
| Sulfolane, Salicylic acid, Acetophenone | $(1/3)^3$ | $(2/5)^3$ | 2.58 | 3.14 |
| Sulfolane, Salicylic acid, Adiponitrile | " | " | 2.88 | 4.08 |
| Sulfolane, Methyl glutaronitrile, Adiponitrile | " | " | 2.59 | 2.94 |
| Sulfolane, Methyl glutaronitrile, Benzophenone | " | " | 2.67 | 3.27 |
| Dimethyl sulfone, Adiponitrile | $(1/2)^2$ | $(3/5)^2$ | 2.65 | 3.64 |
| Dimethyl sulfone, Adiponitrile, Acetophenone | $(1/3)^3$ | $(2/5)^3$ | 3.37 | 2.90 |
| Phenyl sulfone, Adiponitrile | $(1/2)^2$ | $(3/5)^2$ | 2.08 | 1.62 |
| Phenyl sulfone, Adiponitrile, Acetophenone | $(1/3)^3$ | $(2/5)^3$ | 2.73 | 4.58 |
| Dihydroxydiphenylsulfone, Adiponitrile | $(1/2)^2$ | $(3/5)^2$ | 1.92 | 3.32 |
| Dihydroxydiphenylsulfone, Adiponitrile, Acetophenone | $(1/3)^3$ | $(2/5)^3$ | 3.32 | 3.22 |
| Butadiene sulfone, Adiponitrile | $(1/2)^2$ | | 2.21 | — |
| Sulfolane, Acetophenone | " | $(3/5)^2$ | 3.20 | 3.12 |
| Sulfolane, Acetophenone, 2,4-Pentanedione | $(1/3)^3$ | $(2/5)^3$ | 3.06 | 3.30 |

TABLE 2

Data From Run Made In Rectification Column With Sulfolane

| | Wt. % - 1 hr. | Wt. % - 1.5 hrs. |
|---|---|---|
| Overhead - Water | 99.5 | 99.4 |
| Formic Acid | 0.5 | 0.6 |
| Bottoms - Water | 26.1 | 30.5 |
| Formic Acid | 73.9 | 69.5 |
| Relative Volatility | 4.09 | 4.02 |

TABLE 3

Extractive Distillation Agents Containing Adiponitrile

| Compounds | Ratios | | Relative Volatilities | |
|---|---|---|---|---|
| Adiponitrile | 1 | 6/5 | 2.41 | 2.98 |
| Adiponitrile, Acetophenone | $(1/2)^2$ | $(3/5)^2$ | 3.68 | 2.45 |
| Adiponitrile, Benzoic acid | " | " | 5.69 | 2.75 |
| Adiponitrile, Benzonitrile | " | " | 2.57 | 3.63 |
| Adiponitrile, Benzophenone | " | " | 3.24 | 5.13 |
| Adiponitrile, m-Hydroxyacetophenone | " | " | 4.15 | 2.58 |
| Adiponitrile, Methyl glutaronitrile | " | " | 3.01 | 3.92 |

TABLE 3-continued

Extractive Distillation Agents Containing Adiponitrile

| Compounds | Ratios | | Relative Volatilities | |
|---|---|---|---|---|
| Adiponitrile, Propiophenone | " | " | 3.43 | 2.66 |
| Adiponitrile, Salicylic acid | " | " | 1.92 | 3.82 |
| Adiponitrile, Methyl glutaronitrile, Acetophenone | $(1/3)^3$ | $(2/5)^3$ | 7.22 | 11.2 |
| Adiponitrile, Methyl glutaronitrile, Benzonitrile | " | " | 3.97 | 5.55 |
| Adiponitrile, Methyl glutaronitrile, Benzophenone | " | " | 5.98 | 6.34 |
| Adiponitrile, Methyl glutaronitrile, m-Hydroxyacetophenone | " | " | 2.87 | 3.88 |
| Adiponitrile, Methyl glutaronitrile, Propiophenone | " | " | 5.73 | 5.89 |
| Adiponitrile, Methyl glutaronitrile, Salicylic acid | " | " | 4.49 | 8.00 |
| Adiponitrile, Acetamide, Formamide | " | " | 2.97 | 2.07 |
| Adiponitrile, Acetophenone, Benzophenone | " | " | 2.97 | — |
| Adiponitrile, Salicylic acid, Benzonitrile | " | " | 2.94 | 4.66 |
| Adiponitrile, Salicylic acid, Dimethylsulfoxide | " | " | 3.55 | 7.68 |

TABLE 4

Extractive Distillation Agents Containing Methyl Glutaronitrile

| Compounds | Ratios | | Relative Volatilities | |
|---|---|---|---|---|
| Methyl glutaronitrile | 1 | 6/5 | 2.26 | 4.05 |
| Methyl glutaronitrile, Acetophenone | $(1/2)^2$ | $(3/5)^2$ | 3.07 | 7.98 |
| Methyl glutaronitrile, Benzophenone | " | " | 2.69 | 3.35 |
| Methyl glutaronitrile, Propiophenone | " | " | 2.51 | 4.23 |
| Methyl glutaronitrile, Salicylic acid | " | " | 3.24 | 5.72 |
| Methyl glutaronitrile, Acetophenone, 2,4-Pentanedione | $(1/3)^3$ | $(2/5)^3$ | 3.93 | 7.30 |
| Methyl glutaronitrile, Salicylic acid, Benzophenone | " | " | 3.04 | 4.23 |
| Methyl glutaronitrile, Salicylic acid, Propiophenone | " | " | 4.55 | 4.24 |

TABLE 5

Extractive Distillation Agents Containing Dimethylformamide

| Compounds | Ratios | | Relative Volatilities | |
|---|---|---|---|---|
| Dimethylformamide (DMFA) | 1 | 6/5 | 2.75 | 7.95 |
| DMFA, Acetamide | $(1/2)^2$ | $(3/5)^2$ | 6.06 | 9.05 |
| DMFA, 2,4-Pentanedione | " | " | 7.91 | 8.80 |
| DMFA, N,N—Diethylacetamide | " | " | 5.51 | 9.2 |
| DMFA, 2-Methoxyethyl acetate | " | " | 6.50 | 7.63 |
| DMFA, Formamide | " | " | 2.80 | 5.60 |
| DMFA, N—Methylpyrrolidone | " | " | 4.71 | 8.19 |
| DMFA, Ethylene glycol ethyl ether acetate | " | " | 8.26 | 11.1 |
| DMFA, Acetamide, N,N—Dimethylacetamide | $(1/3)^3$ | $(2/5)^3$ | 4.31 | 9.30 |
| DMFA, Acetamide, Formamide | " | " | 9.31 | 9.71 |
| DMFA, Formamide, N—Methyl pyrrolidone | " | " | 8.67 | 8.10 |
| DMFA, Formamide, N,N—Dimethylacetamide | " | " | 7.20 | 5.50 |
| DMFA, N,N—Dimethylacetamide, 2,4-Pentanedione | " | " | 8.57 | 9.46 |
| DMFA, N,N—Dimethylacetamide, 2-Methoxyethyl acet. | " | " | 10.7 | 6.54 |
| DMFA, N,N—Dimethylacetamide, Dimethylsulfoxide | " | " | 6.30 | 8.0 |
| DMFA, N,N—Dimethylacetamide, Ethylene glycol Et ether acetate | " | " | 9.38 | 12.8 |
| DMFA, N,N—Dimethylacetamide, Et. glycol Bu ether acet. | " | " | 5.57 | 12.1 |

TABLE 5-continued

Extractive Distillation Agents Containing Dimethylformamide

| Compounds | Ratios | | Relative Volatilities | |
|---|---|---|---|---|
| DMFA, Ethylene glycol butyl ether acetate | $(1/2)^2$ | $(3/5)^2$ | 4.83 | 10.2 |

TABLE 6

Extractive Distillation Agents Containing Formamide

| Compounds | Ratios | | Relative Volatilities | |
|---|---|---|---|---|
| Formamide | 1 | 6/5 | 10.3 | 11.5 |
| Formamide, Acetamide | $(1/2)^2$ | $(3/5)^2$ | 6.36 | 8.5 |
| Formamide, N—Methyl pyrrolidone | " | " | 5.22 | 9.33 |
| Formamide, N—Methyl pyrrolidone, Acetamide | $(1/3)^3$ | $(2/5)^3$ | 9.52 | 10.4 |
| Formamide, N—Methyl pyrrolidone, N,N—Dimethylacetamide | " | " | 4.80 | 4.23 |

TABLE 7

Extractive Distillation Agents Containing N,N—Dimethylacetamide

| Compounds | Ratios | | Relative Volatilities | |
|---|---|---|---|---|
| N,N—Dimethylacetamide | 1 | 6/5 | 7.47 | 11.3 |
| N,N—Dimethylacetamide, Acetamide | $(1/2)^2$ | $(3/5)^2$ | 5.78 | 10.8 |
| N,N—Dimethylacetamide, Dimethylsulfoxide | " | " | 5.0 | 12.9 |
| N,N—Dimethylacetamide, Formamide | " | " | 7.2 | 10.4 |

TABLE 8

Miscellaneous Effective Extractive Distillation Agents

| Compounds | Ratios | | Relative Volatilities | |
|---|---|---|---|---|
| Acetamide, N—Methylpyrrolidone | $(1/2)^2$ | $(3/5)^2$ | 4.21 | 4.7 |
| Acetophenone | 1 | 6/5 | 2.62 | 4.11 |
| Acetophenone, 2,4-Pentanedione | $(1/2)^2$ | $(3/5)^2$ | 2.87 | 3.17 |
| Acetophenone, Salicylic acid | " | " | 4.10 | 5.18 |
| Benzonitrile, Salicylic acid | " | " | 1.93 | 1.92 |
| N—Methylpyrrolidone | 1 | 6/5 | 6.05 | 8.9 |

THE USEFULNESS OF THE INVENTION

The usefulness or utility of this invention can be demonstrated by referring to the data presented in Tables 1-8. All of the successful extractive distillation agents show that formic acid and water can be separated from their maximum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity formic acid from any mixture with water including the maximum azeotrope. The stability of the compounds used and the boiling point difference is such that complete recovery and recycle is obtainable by a simple distillation and the amount required for make-up is small. The working examples below will show that when the formic acid-water mixture contains an impurity or a mixture of impurities that are soluble in formic acid, soluble in formic acid-water mixtures but insoluble in water, the method described here will remove them from the formic acid by bringing them off overhead with the water. Upon condensation, the water and impurity form to liquid layers which are readily separated by decantation.

WORKING EXAMPLES

1. Fifty grams of the formic acid-water azeotrope, fifty grams of sulfolane and five grams of methyl t-butyl ether were charged to an Othmer type glass vapor-liquid equilibrium still and refluxed for five hours. Analysis of the vapor and liquid by gas chromatography gave a vapor composition of 36% water, 64% formic acid; a liquid composition of 21% water, 79% formic acid. This indicates a relative volatility of 2.11. Ten grams of sulfolane and five grams of methyl t-butyl ether were added and refluxing continued for another fourteen hours. Analysis indicated a vapor composition of 37.5% water, 62.5% formic acid; a liquid composition of 18.5% water, 81.5% formic acid which is a relative volatility of 2.04. In each case, the methyl t-butyl ether came off first with the water, formed two layers and was decanted.

EXAMPLE 2

Fifty grams of the formic acid-water azeotrope, 25 grams of sulfolane, 25 grams of adiponitrile and five grams of diisopropyl ether were charged to the vapor-liquid equilibrium still and refluxed for ten hours. Analysis indicated a vapor composition of 34% water, 66% formic acid; a liquid composition of 12% water, 88% formic acid which is a relative volatility of 3.28. Five grams of sulfolane, five grams of adiponitrile and five grams of diisopropyl ether were added and refluxing continued for another twelve hours. Analysis indicated a vapor composition of 40% water, 60% formic acid; a liquid composition of 14.5% water, 85.5% formic acid which is a relative volatility of 3.93. In each case the diisopropyl ether came off first with the water, formed two layers and was decanted.

EXAMPLE 3

Fifty grams of the formic acid-water azeotrope, 17 grams of dimethylsulfone, 17 grams of adiponitrile, 17 grams of acetophenone and five grams of n-butyl acetate were charged to the vapor-liquid equilibrium still and refluxed for eleven hours. Analysis indicated a vapor composition of 40% water, 60% formic acid; a liquid composition of 16.5% water, 83.5% formic acid which is a relative volatility of 3.37. Three grams each of dimethylsulfone, adiponitrile, acetophenone and three grams of acetonyl acetone were added and refluxing continued for another twelve hours. Analysis indicated a vapor composition of 42% water, 58% formic acid; a liquid composition of 20% water, 80% formic acid which is a relative volatility of 2.90. In each case, the n-butyl acetate and the acetonyl acetate came off first with water, formed two layers and was separated from the water by decantation.

EXAMPLE 4

A glass perforated plate rectification column was calibrated with ethylbenzene and p-xylene which possesses a relative volatility of 1.06 and found to have 4.5 theoretical plates. A solution comprising 340 grams of formic acid and 60 grams of water was placed in the stillpot and heated. When refluxing began, an extractive agent consisting of adiponitrile was pumped into the column at a rate of 20 ml/min. The temperature of the extractive agent as it entered the column was 46° C. After establishing the feed rate of the extractive agent, the heat input to the formic acid and water in the stillpot was adjusted to give a total reflux rate of 10-20 ml/min. After one hour of operation, the overhead and bottoms samples of approximately two ml. were collected and analysed using gas chromatography. The overhead analysis was 99.5% water, 0.5% formic acid. The bottoms analysis was 68.6% water, 31.4% formic acid. Using these compositions in the Fenske equation, with the number of theoretical plates in the column being 4.5, gave an average relative volatility of 2.73 for each theoretical plate. After one and a half hours of total operating time, the overhead and bottoms samples were again taken and analysed. The overhead composition was 99.5% water, 0.5% formic acid and the bottoms composition was 70% water, 30% formic acid. This gave an average relative volatility of 2.69 for each theoretical plate. Five grams of diisobutyl ketone were added to the stillpot. Five minutes later, the diisobutyl ketone came off overhead as a two phase liquid with the water.

EXAMPLE 5

Fifty grams of a commercial acid mixture containing 35% water, 25% formic acid, 35% acetic acid and 5% benzene was mixed with 50 grams of N,N-dimethylacetamide, charged to the vapor-liquid equilibrium still and refluxed for ten hours. The benzene immediately came off overhead and formed an insoluble liquid layer above the water and was decanted and removed from the system. Analysis gave a vapor composition of 80.9% water, 5.6% formic acid and 13.5% acetic acid; a liquid composition of 36.5% water, 27% formic acid and 36.5% acetic acid. This gives a relative volatility of water to formic acid of 10.6.

We claim:

1. A method for recovering impurity-free formic acid from mixtures of formic acid, water and impurities that are soluble in formic acid and formic acid-water mixtures but insoluble in water, which comprises distilling a mixture of formic acid, water and impurities in a rectification column in the presence of about one part of an extractive agent per part of formic acid-water-impurity mixture, recovering water and the impurity as an overhead product which on condensation separates into two liquid layers, and obtaining the formic acid and the extractive agent from the stillpot, wherein said extractive agent is selected from at least one member of the group consisting of adiponitrile, sulfolane, methyl glutaronitrile and acetophenone.

2. A method for recovering impurity-free formic acid from mixtures of formic acid, water and impurities that are soluble in formic acid and formic acid-water mixtures but insoluble in water, which comprises distilling a mixture of formic acid, water and impurities in a rectification column in the presence of about one part of an extractive agent per part of formic acid-water impurity mixture, recovering water and the impurity as an overhead product which on condensation separates into two liquid layers, and obtaining the formic acid and extractive agent from the stillpot, wherein said extractive agent is selected from mixtures consisting of at least two materials selected from the group consisting of adiponitrile, methyl glutaronitrile, sulfolane, dimethyl sulfone, phenyl sulfone, dihydroxydiphenyl sulfone, butadiene sulfone, acetophenone, benzophenone, m-hydroxyacetophenone, propiophenone, salicylic acid, phenyl acetic acid, benzoic acid, benzonitrile, dimethylsulfoxide, 2,4-pentanedione, 2-methoxyethyl acetate, ethylene glycol ethyl ether acetate and ethylene glycol butyl ether acetate.

* * * * *